United States Patent [19]

Sarstedt

[11] Patent Number: 4,722,352

[45] Date of Patent: * Feb. 2, 1988

[54] BLOOD EXTRACTION DEVICE

[75] Inventor: Walter Sarstedt, Nümbrecht-Rommelsdorf, Fed. Rep. of Germany

[73] Assignee: Walter Sarstedt Kunststoff-Spritzgusswerk, Fed. Rep. of Germany

[*] Notice: The portion of the term of this patent subsequent to Jul. 17, 2001 has been disclaimed.

[21] Appl. No.: 874,816

[22] Filed: Jun. 12, 1986

Related U.S. Application Data

[63] Continuation of Ser. No. 669,195, Nov. 7, 1984, abandoned.

[30] Foreign Application Priority Data

Nov. 15, 1983 [DE] Fed. Rep. of Germany ....... 3341360

[51] Int. Cl.$^4$ ................................................ A61B 5/00
[52] U.S. Cl. ..................................................... 128/765
[58] Field of Search ........................ 128/763, 744, 765; 604/199, 221, 222

[56] References Cited

U.S. PATENT DOCUMENTS

| 2,742,041 | 4/1956 | Lipari | 128/765 |
| 3,013,557 | 12/1961 | Pallotta | 128/765 |
| 3,485,239 | 12/1969 | Vanderbeck | 604/199 X |
| 3,577,980 | 5/1971 | Cohen | 128/765 |
| 3,937,211 | 2/1976 | Merten | 128/765 |
| 4,012,325 | 3/1977 | Columbus | 128/764 X |
| 4,030,498 | 6/1977 | Tompkins | 604/221 X |
| 4,459,997 | 7/1984 | Sarstedt | 128/765 X |

FOREIGN PATENT DOCUMENTS

| 2653206 | 6/1977 | Fed. Rep. of Germany. |
| 2948653 | 6/1981 | Fed. Rep. of Germany. |
| 3005679 | 8/1981 | Fed. Rep. of Germany ...... 128/763 |

Primary Examiner—Edward M. Coven
Attorney, Agent, or Firm—Townsend and Townsend

[57] ABSTRACT

A blood extraction device includes a sample extraction tube having an open rear end and a first sealing surface at the rear end. A piston assembly includes a piston removably housed within the tube for movement between a retracted position toward the rear end and an extended position. The piston assembly also includes a piston rod portion extending through the open rear end of the tube. The piston rod portion has a reduced diameter portion along a substantial part of its length and an enlarged portion which defines a second sealing surface for complementary mating engagement with the first sealing surface when the piston is at its extended position. The piston is locked in its fully retracted position by the engagement of a forwardly facing annular flange on the piston assembly and a rearwardly facing annular step of the tube. Preferably the piston assembly includes a frangible joint to permit at least a part of the piston rod portion to be separated from the piston after the piston is in the retracted position.

25 Claims, 2 Drawing Figures

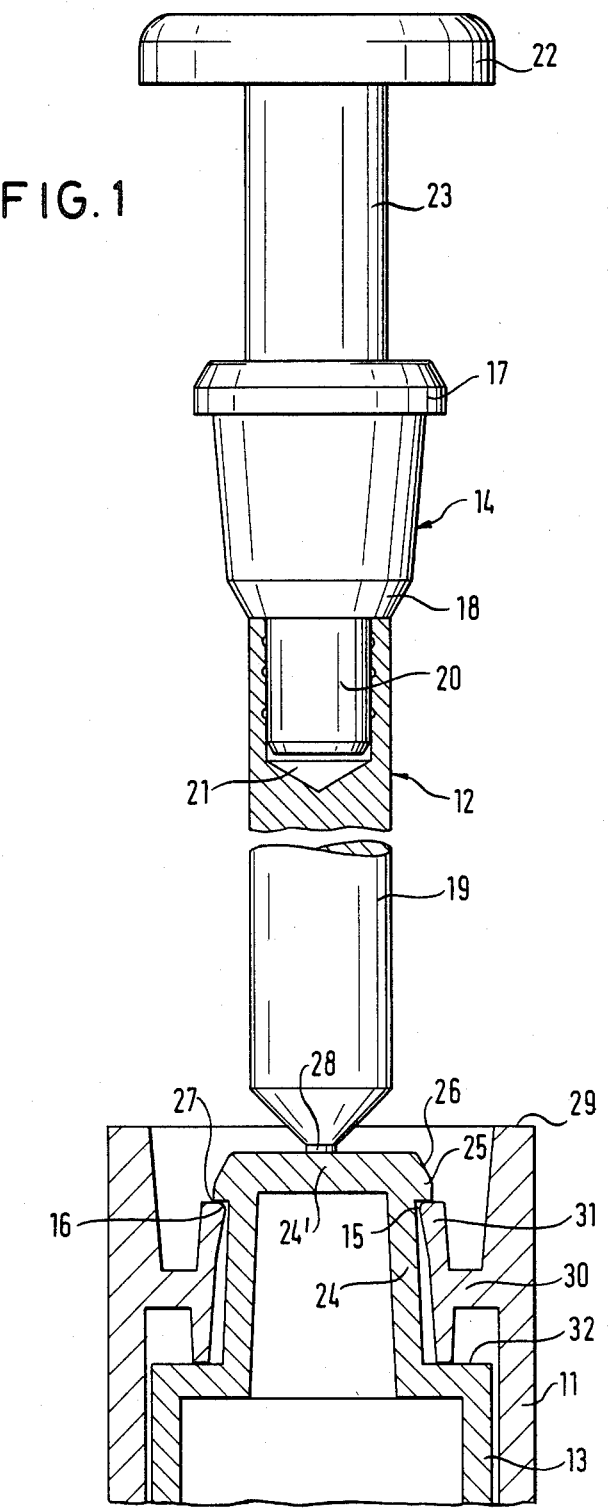

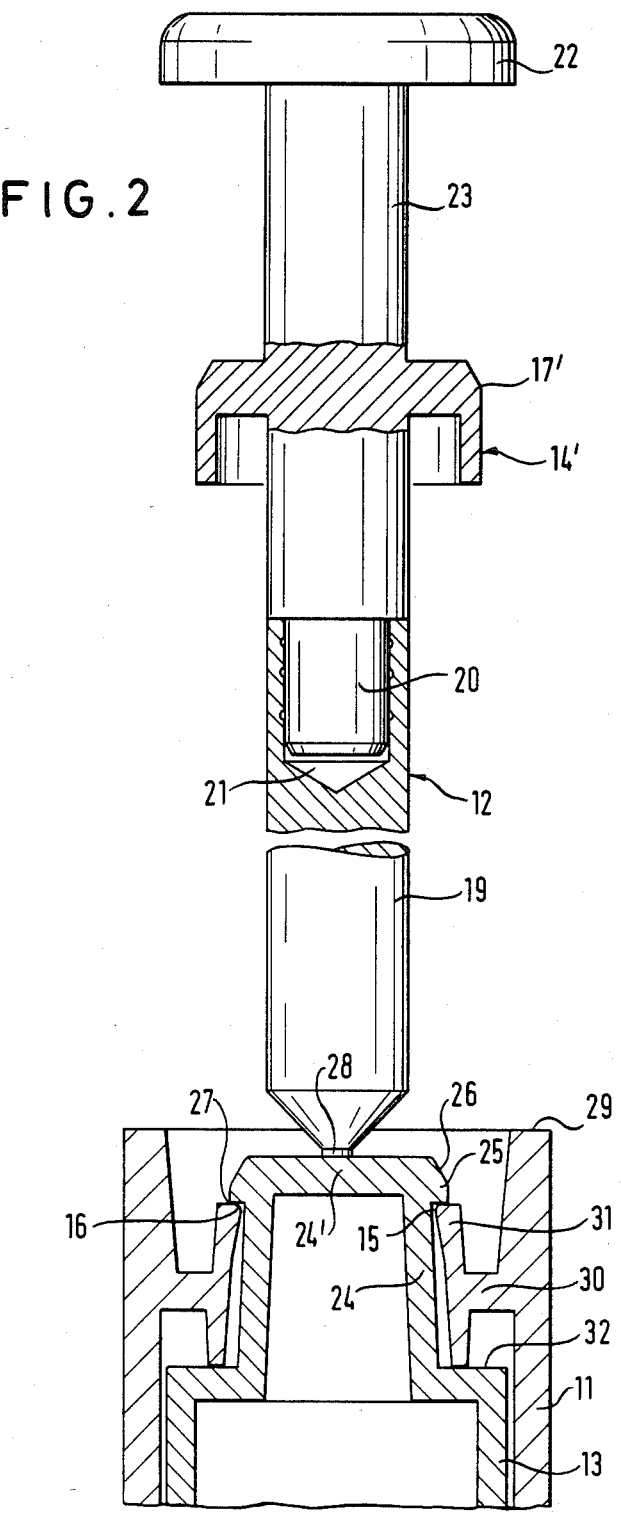

BLOOD EXTRACTION DEVICE

This is a continuation of Ser. No. 669,195, filed Nov. 7, 1984, now abandoned.

The invention relates to a blood extraction device comprising a cylindrical sample extraction tube containing a piston, wherein the one end of the sample extraction tube is hermetically sealed against the outside environment by a closure cap, and wherein the other end of the sample extraction tube has an opening for the movement therethrough of a piston rod connected to the piston.

In order to keep the interior of the sample extraction tubes of such blood extraction devices sterile against external influences, while nevertheless providing access to the interior, the closure cap generally has a closure plug which can be punctured by the sharpened rear end of a cannula (see for example German Auslegeschrift DE-AS No. 26 53 206). The end of the sample extraction tube having the opening for the piston rod can be sealed if the diameter of the opening is made to correspond to the diameter of the piston rod (German Patent DE-PS No. 24 56 561). It is however a disadvantage of this construction that the sealed guiding of the piston rod during sliding movement prevents the escape of air present between the piston rod and the cylinder during the drawing of blood or the generation of a vacuum. For this reason it is customary to leave a considerable ring gap between the piston rod and the end of the sample extraction tube through which it passes so that the air present between the piston and the sample extraction tube can escape through the ring gap during the drawing of blood or the generation of a vacuum in the sample extraction tube (German Offenlegungsschrift DE-OS No. 30 26 281).

If one now wishes to keep the blood extraction devices of the initially named kind absolutely sterile under extreme conditions then it is necessary to pack the sample extraction tubes in hermetically sealed bubbles which, on the one hand, is relatively costly and, on the other hand, makes the blood extraction device more difficult to use.

The object of the present invention is thus to provide a blood extraction device of the initially named kind the interior of which can be kept sterile even under extreme conditions without requiring sterile packaging and without preventing the escape of air on retraction of the piston.

In order to satisfy this object the invention provides that the piston rod is hermetically sealingly connected with the sample extraction tube by a releasable sealed connection but only at the point at which, with the piston advanced, it passes through the other end of the sample extraction tube.

The thought underlying the invention is thus to select the diameter of the greater part of the piston rod to be substantially smaller than the diameter of the opening at the end of the sample extraction tube through which the piston rod passes. When the piston has been fully advanced in the forward direction a hermetic seal is however effective between the piston rod and the opening of the sample extraction tube and makes the penetration of germs impossible during storage and up until the device is used, even under extreme conditions.

A particularly preferred constructional realisation of the blood extraction device of the invention is characterised in that the releasable sealed connection is formed by a thickened region of the piston rod at the point at which, with the piston advanced, the piston rod passes through the other end of the sample extraction tube, and by an opening complementary to the thickened portion at said other end of the sample extraction tube, with the thickened region being in lightly clamped sealing engagement with the edge of the opening when the piston is advanced. When the piston is advanced the conical thickened portion thus clamps itself into the opening whereby an absolutely sealed closure of the inner chamber of the sample extraction tube is obtained at the side of the piston remote from the closure cap. The sealed connection can be simply and fully released during use by pulling the thickened portion out of the opening so that the escape of air present behind the piston is not hindered during the drawing of blood or during the generation of vacuum by retraction of the piston.

The sealing action in the advanced state of the piston can be improved if the conical thickened region has a flange at the end remote from the sample extraction tube which can, if necessary, additionally contact the edge of the opening.

The introduction of the conical thickened region into the opening can be simplified, even if the piston rod is bent somewhat in a sideways direction, if, in accordance with a further embodiment, the conical thickened region merges, at the end facing the sample extraction tube, via a shallow lead-in ramp into a cylindrical piston rod part of smaller diameter which leads to the piston.

In order to obtain completely burr-free sealing surfaces at the conical thickened region a further development of the invention provides that a preferably cylindrical spigot projects axially from the tapered end of the thickened region into a complementary blind bore in the rear end face of the cylindrical part of the piston rod and is secured there. In this manner the thickened region can be manufactured with a one piece mould and is subsequently fixedly connected to the piston rod part provided on the piston.

In accordance with a further embodiment a further piston rod part of reduced diameter is provided between the conical thickened region and a knob at the rear end of the piston rod. The diameter of this piston rod part is expediently the same as the diameter of the piston rod part located between the thickened region and the piston. As a result of this construction the handling of the blood extraction device is not made more difficult despite the presence of the conical thickened region.

In order to latch the piston in the retracted position so as to maintain a vacuum generated during the retraction a preferably slightly conically tapered projection should be provided at the rear end of the piston and should have an annular flange at its rear end, with the annular flange having a lead-in ramp at the end remote from the piston by means of which it can be resiliently coerced to pass through the opening; and an annular step forming a seat for the annular flange should adjoin the edge of the opening radially outwardly. The piston rod is expediently connected with the rear end of the projection via a desired fracture point in order that the piston rod can be removed after retraction and latching of the piston. The annular step and the desired fracture point should be arranged axially inside the rear end face of the sample extraction tube, i.e. in recessed manner, so that the sample extraction tube can be handled without hinderance after removal of the piston rod and can for example be arranged in a centrifuge.

The invention will now be described in the following by way of example and with reference to the drawing in which there is shown:

FIG. 1 a partly sectioned side view of the rear part of a blood extraction device in accordance with the invention, and FIG. 2 a corresponding side view of a modified embodiment.

As seen in FIG. 1 a sample extraction tube 11 has a radially inwardly projecting flange 30 at an axial distance from the rear end face 29. A tubular element 31 which tapers somewhat conically in a rearward direction is moulded onto the flange 30.

The front end (not shown) of the sample extraction device 11 is hermetically sealed by a closure cap which can have puncturable closure plug for the insertion of the rear end of a cannula which is sharpened at both ends.

A piston 13 is axially displaceably arranged inside the sample extraction tube 11. At its rear end the piston 13 has a projection 24 which is gently conically tapered in a rearward direction and which, like the piston, is of hollow construction. The rear end of the projection 24 terminates in a flat plate part 24' so that the annular step 32 provided between the piston 13 and the projection 24 axially contacts the conical tubular element 31 when the piston is fully retracted.

A radially outwardly projecting annular flange 25, which is provided with a lead-in chamfer 26 at its end remote from the piston 13, is located at the rear end of the projection 24. The lead-in chamfer makes it possible for the flange 25 to force its way through the opening 15 at the rear end of the tubular element 31 and for the annular flange 25 to snap over the annular step 27 provided at the end of the tubular element 31.

A cylindrical piston rod part 19 of the piston rod 12 is connected with the plate 24' of the projection 24 via a desired fracture point or frangible neck 28. At the end remote from the piston 13 the piston rod part 19 has a blind bore 21 in its rear end face into which a spigot 20 of a conically thickened region 14 of the piston rod 12 is inserted. The spigot 20 can be secured in the blind bore 21, for example by adhesive. Making piston rod 12 from two parts allows the part including thickened region 14 to be made with a one piece mold to eliminate any parting lines over the sealing surface. This provides a smooth sealing surface, one not obtainable if piston rod 12 and piston 13 were molded as a unitary item in a two piece mold. A lead-in chamfer 18 is provided between the thickened region 14 and the piston rod part 19. The rear end of the thickened region 14 is constructed as an annular flange 17 to which once again a cylindrical piston rod part 23 of the same diameter as the piston rod part 19 is attached and which extends to the knob 22.

Whereas the diameter of the piston rod part 19 is significantly smaller than the diameter of the opening 15 at the end of the sample extraction tube 11, the thickened region 14 has a somewhat smaller diameter than the opening 15 at its front region and a somewhat larger diameter than the opening 15 at its rear region. In this manner the conical thickened region 14 comes into contact with the end 16 of the opening 15 when the piston is advanced into the frontmost position which is not shown in the drawing. By pushing the thickened region 14 into the opening 15 under gentle pressure it is possible to obtain a lightly clamped and hermetically sealed seat between the thickened region 14 and the edge 16. In order to improve the sealing action the edge 16 is lightly rounded at the rear end of the conical tubular element 31 in order to form a type of sealing bead.

In this manner the interior of the sample extraction tube 11 can be completely hermetically sealed against the outside environment until it is used so that any penetration of germs is effectively avoided.

In use it is only necessary to draw to the knob 22 gently in a rearward direction in order to release the sealed connection between the thickened region 14, which is only slightly conically shaped, and the edge 16. The air located between the piston rod and the sample extraction tube 11 can now easily escape during retraction of the piston through the gap present between the piston rod part 19 of reduced diameter and the edge 16.

At the end of the retraction movement the flange 15 snaps behind the annular step 27 whereby the piston 13 is fixed once and for all in the position shown in the drawing which again likewise results in complete sealing of the sample extraction tube in the region of the opening 15. The piston rod 12 is now broken off from the projection 24 on the piston 13 in the region of the desired fracture point 28. As the desired fracture point 28 is arranged in recessed manner relative to the rear end face 29 of the sample extraction tube 11, no parts any longer project axially in a rearward direction beyond the sample extraction tube 11. The sample extraction tube 11 can thus be straightforwardly handled together with its contents and for example placed on a flat surface or into a centrifuge in the reversed position to that shown in the drawing.

The cone angle of the thickened region 14 is preferably approximately 3°.

If desired the flange 17 can also be of somewhat conical construction in accordance with the thickened region 14, and indeed in such a way that the cone sealingly contacts the internal opening provided at the rear end face 29. The single hermetic seal between the piston and the sample extraction tube 11 could also be provided at this point. In this case the thickened region 14 is not necessary. Instead this region could have the same diameter as the piston rod parts 19, 23.

The thickened region 14 could, if desired, have the cone angle 0° as a boundary value.

In the embodiment of FIG. 2 the same reference numerals are used to designate parts having counterparts in FIG. 1. In distinction to FIG. 1 an annular sealing cap 14' is provided at the piston rod flange 17' which, with the piston 13 advanced, is pushed over the somewhat conical tubular element 31 which forms the rearwardly directed projection and sealingly engages the same.

In principle the sealing cap could also have a larger diameter and sealingly engage the rear end of the sample extraction tube 11 in the region of the end face 29. The thickened region 14 of the embodiment of FIG. 1 is thus replaced here by the covering cap 14'.

The flange 17, 17' in the two embodiments also has the important function that it determines the initial position of the suction piston 13 by abutment on the tubular element 31 before the piston is retracted into the position shown in the drawing.

Finally, it should be pointed out that the cylindrical spigot 20 could also project upwardly or rearwardly from the cylindrical part 19 and indeed into a complementary blind bore in the thickened region 14. This reversed arrangement of the cylindrical spigot 20 when compared with FIGS. 1 and 2 would have the advantage that the wall thickness around the blind bore 21 would be larger and the entire arrangement would thus be more stable.

I claim:

1. A blood extraction device comprising:

a sample extraction tube having an open rear end and a first sealing surface at the rear end;

a piston assembly including a piston, housed within the tube for movement between a retracted position toward the open rear end and an extended position, and a piston rod portion extending through the open rear end of the tube;

the piston rod portion having an enlarged portion defining a second sealing surface for complementary mating engagement with the first sealing surface when the piston is at the extended position; and means for retaining the piston in the retracted position against any movement away from the rear end by any vacuum in the tube, the retaining means including:

a rearwardly facing annular step at the open rear end of the tube; and a forwardly facing flange carried by the piston assembly, at least one of the annular step and annular flange being a radially yieldable, the annular step and annular flange sized to engage one another when the piston is moved into the retracted position, during which said at least one step and flange is deflected radially, to prevent the piston from moving toward the extended position.

2. The device of claim 1 wherein the piston has a reduced diameter portion with a cross-sectional size substantially smaller than the first sealing surface over a substantial part of its length.

3. The device of claim 2 wherein the reduced diameter portion includes first and second parts on either side of the enlarged portion, the first part being between the enlarged portion and the piston, and wherein the piston rod portion including a knob attached to the second part.

4. The device of claim 1 wherein the first sealing surface is an inwardly facing surface defining an opening through which the piston rod portion passes.

5. The device of claim 4 wherein the second sealing surface is a conical surface.

6. The device of claim 1 wherein the enlarged portion includes a flange for abutment against the annular step when the piston assembly is in the extended position.

7. The device of claim 1 wherein the first sealing surface is a radially outwardly facing surface.

8. The device of claim 1 wherein the tube includes a sidewall portion and a tubular element therein and wherein the first sealing surface and the annular step are both part of the tubular element.

9. The device of claim 1 wherein the tube includes a sidewall portion and a tubular element therein.

10. The devices of claim 9 wherein the annular step is a part of the tubular element.

11. The device of claim 10 wherein the tubular element is connected to the sidewall portion by an inwardly projecting flange.

12. The device of claim 11 wherein the inwardly projecting flange is positioned medially along the tubular element.

13. The device of claim 1 wherein the piston assembly includes a lead-in chamfer, adjacent the forwardly facing annular flange, tapering inwardly and rearwardly to aid engagement of the annular step and annular flange.

14. The device of claim 1 wherein the piston assembly includes a frangible portion to permit at least a part of the piston rod portion to be separated from the piston after the piston is in the retracted position.

15. The device of claim 14 wherein the frangible portion is near but forward of the open rear end of the tube when the piston is in the retracted position.

16. The device of claim 1 wherein the piston rod portion is a two part assembly coupled by a joint between the enlarged portion and the piston having a spigot portion and a complementary opening within which the spigot is secured so that the part of the piston rod portion including the enlarged portion can be made in a one-piece mold.

17. A blood extraction device comprising:

a sample extraction tube having an open rear end and a first, radially inwardly facing annular sealing surface at the rear end, the first sealing surface defining an opening:

a piston assembly including a piston, housed within the tube for movement between a retracted position toward the open rear end and an extended position, and a piston rod portion extending through the opening at the rear end of the tube;

the piston rod portion having an enlarged portion defining a second, conical sealing surface for complementary mating engagement with the first sealing surface when the piston is at the extended position;

the tube including a rearwardly facing annular step at the open rear end of the tube; and the piston assembly including a forwardly facing flange, at least one of the annular step and annular flange being a radially yieldable, the annular step and annular flange sized to engage one another when the piston is moved into the retracted position, during which said at least one step and flange is deflected radially, to prevent the piston from moving toward the extended position.

18. The device of claim 17 wherein:

the tube includes a sidewall portion and a tubular element, the tubular element being connected to the sidewall portion by an inwardly projecting flange positioned medially along the tubular element; and the annular step is a part of the tubular element.

19. The device of claim 18 wherein the piston assembly includes a frangible portion to permit at least a part of the piston rod portion to be separated from the piston after the piston is in the retracted position, the frangible portion being near but slightly forward of the open rear end of the tube when the piston is in the retracted position.

20. The device of claim 19 wherein the piston rod portion is a two part assembly coupled by a joint, located between the enlarged portion and the frangible portion, having a spigot portion and a complementary opening within which the spigot is secured so that the part of the piston rod portion including the enlarged portion can be made in a one-piece mold.

21. A blood extraction device comprising:

a sample extraction tube having an open rear end and a first, radially outwardly facing sealing surface at the rear end;

a piston assembly including a piston, housed within the tube for movement between a retracted position toward the open rear end and an extended position, and a piston rod portion extending through the open rear end of the tube;

the piston rod portion having an enlarged portion defining a second sealing surface for complementary mating engagement with the first sealing surface when the piston is at the extended position;

the tube including a rearwardly facing annular step at the open rear end of the tube;

the piston assembly including a forwardly facing flange carried by the piston assembly, at least one of the annular step and annular flange being a radially yieldable, the annular step and annular flange sized to engage one another when the piston is moved into the retracted position, during which said at least one step and flange is deflected radially, to prevent the piston from moving toward the extended position; and the tube including a sidewall portion and a tubular element therein, the first sealing surface and the annular step both being part of the tubular element.

22. The device of claim 21 wherein the tubular element is connected to the sidewall portion by an inwardly projecting flange.

23. The device of claim 22 wherein the piston assembly includes a frangible portion to permit at least a part of the piston rod portion to be separated from the piston after the piston is in the retracted position, the frangible portion is near but slightly forward of the open rear end of the tube when the piston is in the retracted position.

24. The device of claim 23 wherein the piston rod portion is a two part assembly coupled by a joint having a spigot portion and a complementary opening within which the spigot is secured so that the part of the piston rod portion including the enlarged portion can be made in a one-piece mold.

25. A blood extraction device comprising:

a sample extraction tube having an open rear end and a first, radially outwardly facing sealing surface at the rear end, the tube including a sidewall portion and a tubular element therein, the tubular element being connected to the sidewall portion by an inwardly projecting flange;

a piston assembly including a piston, housed within the tube for movement between a retracted position toward the open rear end and an extended position, and a piston rod portion extending through the open rear end of the tube;

the piston rod portion having an enlarged portion defining a second sealing surface for complementary mating engagement with the first sealing surface when the piston is at the extended position;

the tube including a rearwardly facing annular step at the open rear end of the tube, the annular step being a part of the tubular element;

the piston assembly including a forwardly facing flange carried by the piston assembly, at least one of the annular step and annular flange being a radially yieldable, the annular step and annular flange sized to engage one another when the piston is moved into the retracted position, during which said at least one step and flange is deflected radially, to prevent the piston from moving toward the extended position under the influence of any vacuum in the tube;

the piston assembly including a frangible portion to permit at least a part of the piston rod portion to be separated from the piston after the piston is in the retracted position, the frangible portion being near but forward of the open rear end of the tube when the piston is in the retracted position; and the piston rod portion being a two part assembly coupled by a joint, located between the enlarged portion and the frangible portion, having a spigot portion and a complementary opening within which the spigot is secured so that the part of the piston rod portion including the enlarged portion can be made in a one-piece mold.

* * * * *